United States Patent

Cairns et al.

Patent Number: 5,286,722
Date of Patent: Feb. 15, 1994

[54] TETRAHYDROPYRIDINYLDIBENZAZEPINE DERIVATIVES

[75] Inventors: James Cairns, Cumbernauld; Samuel G. Gibson; Duncan R. Rae, both of Lanarkshire, all of Scotland

[73] Assignee: AKZO N.V., Arnhem, Netherlands

[21] Appl. No.: 982,259

[22] Filed: Nov. 25, 1992

Related U.S. Application Data

[63] Continuation of Ser. No. 734,824, Jul. 24, 1991, abandoned.

[30] Foreign Application Priority Data

Jul. 24, 1990 [EP] European Pat. Off. ........ 90308071.1

[51] Int. Cl.$^5$ ................. A61K 31/55; C07D 267/20; C07D 281/16; C07D 498/04
[52] U.S. Cl. ............................... 514/211; 540/547; 540/548
[58] Field of Search ................. 540/547, 548; 514/211

[56] References Cited

U.S. PATENT DOCUMENTS

| | | | |
|---|---|---|---|
| 3,501,483 | 3/1970 | Howell et al. | 540/547 |
| 4,221,714 | 9/1980 | McKenzie et al. | 540/547 |
| 4,929,734 | 5/1990 | Coughenour et al. | 546/338 |

OTHER PUBLICATIONS

P. Seeman et al., "Dopamine receptors in human and calf brains, using [H$^3$] apomorphine and an antipsychotic drug," Proc. Natl. Acad. Sci., vol. 73 No. 12, pp. 4354-4358, Dec. 1976, USA.
Henry I. Yamamura et al., "Muscaranic Cholinergic Binding in Rat Brain," Proc. Natl. Acad. Sci., vol. 71, No. 5, pp. 1725-1729, May 1974, USA.
M. Titeler et al., "Multiple receptors for brain dopamine," Proc. Natl. Acad. Sci., vol. 75, No. 3, pp. 1153-1156, Mar. 1978, USA.
Pamela Greengrass et al., "Binding Characteristics of $^3$H-Prazosin to Rat Brain a-Adrenergic Receptors," European Journal of Pharmacology, 55(1979) pp. 323-326, The Netherlands.
P. Protais et al., "Climbing Behavior Induced by Apomorphine in Mice: A Simple Test for the Study of Dopamine Receptors in Striatum," Psychopharmacology, vol. 50, pp. 1-6, 1976.
George Battaglia et al., "Properties of [$^3$H] Prazosin-Labeled al-Adrenergic Receptors in Rat Brain and Porcine Neurointermeiate Lobe Tissue," Journal of Neurochemistry, vol. 41, No. 2, 1983, pp. 538-542.

Primary Examiner—Emily Bernhardt
Assistant Examiner—Philip I. Datlow
Attorney, Agent, or Firm—William M. Blackstone

[57] ABSTRACT

The invention relates to tetrahydropyridinyldibenzazepine derivatives of the formula I

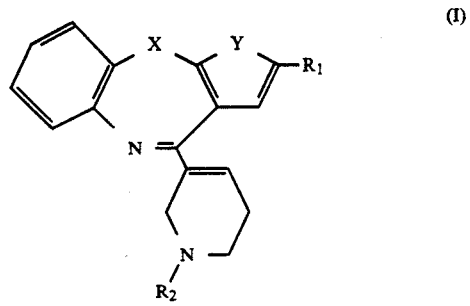

wherein
$R_1$ is a substituent selected from the group consisting of hydrogen, halogen, and lower alkyl;
$R_2$ is selected from hydrogen, and unsubstituted or hydroxy substituted lower alkyl or lower alkenyl;
X is O, S, or $CH_2$;
Y is HC=CH or S;

or a pharmaceutically acceptable salt thereof.

These compounds are dopamine antagonists and are therefore useful for the treatment of psychotic disorders such as schizophrenia, schizophreniform disorder, delusional disorder, acute manic states, senile and presenile psychotic states, toxic psychoses, psychoactive-substance induced psychoses, symptoms of severe restlessness, hyperexcitability and anxiety, motor disorders, among which Tourette's disorder and Huntington's chorea, nausea and vomiting, hiccup and dizziness.

6 Claims, No Drawings

TETRAHYDROPYRIDINYLDIBENZAZEPINE DERIVATIVES

This is a continuation of application Ser. No. 07/734,824 filed Jul. 24, 1991, now abandoned.

The invention relates to tetrahydropyridinyldibenzazepine derivatives of formula I

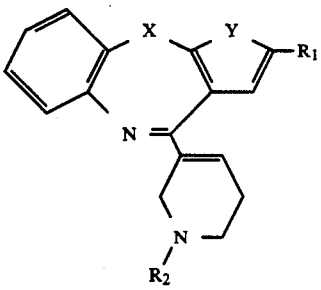

(I)

wherein
$R_1$ is a substituent selected from the group consisting of hydrogen, halogen, and lower alkyl;
$R_2$ is selected from hydrogen, and unsubstituted or hydroxy substituted lower alkyl or lower alkenyl;
X is O, S, or $CH_2$;
Y is HC=CH or S; or a pharmaceutically acceptable salt thereof.

These compounds are dopamine antagonists, and are therefore useful for the treatment of psychotic disorders such as schizophrenia, schizophreniform disorder, delusional disorder, acute manic states, senile and presenile psychotic states, toxic psychoses, psychoactive-substance induced psychoses, symptoms of severe restlessness, hyperexcitability and anxiety, motor disorders, among which Tourette's disorder and Huntington's chorea, nausea and vomiting, hiccup and dizziness.

Related compounds are known from U.S. Pat. No. 4,221,714, which differ from the present compounds in having a 4-tetrahydropyridinyl group, instead of a 3-tetrahydropyridinyl group. All the compounds disclosed in said patent are, moreover, 8-chloro derivatives, whereas the corresponding aromatic ring in the present compounds is unsubstituted. These prior art compounds are claimed as antipsychotic agents, but are known to have cardiovascular and extra-pyramidal side-effects. The compounds of formula I have lower affinity to $\alpha_1$-adrenergic receptors, and a more favourable binding to dopamine $D_2$ receptors than to $\alpha_1$-adrenergic receptors (spiperoneprazosin binding ratio) than the corresponding prior art compounds, indicating that the compounds of the invention exhibit less cardiovascular side-effects, especially less orthostatic hypotension. Most of the compounds of this invention, moreover, show significant improvements by having stronger binding to muscariniccholinergic than to dopamine $D_2$ receptors (as demonstrated by the 3-quinuclidinyl benzilate and spiperone binding affinities), which results in less extra-pyramidal side-effect. The compounds of this invention, thus, have fewer cardiovascular, and mostly also fewer extra-pyramidal side-effects.

The term halogen used in the definition of formula I means fluorine, chlorine, bromine or iodine. Chlorine is the preferred halogen.

The term lower alkyl means a branched or unbranched alkyl group with preferably 1-4 carbon atoms, such as methyl, ethyl, propyl, isopropyl, butyl, tert-butyl and the like. Preferred alkyl groups are methyl and ethyl.

The term lower alkenyl means a branched or unbranched aliphatic hydrocarbon group with 2-6 carbon atoms having a double bond. Examples are ethenyl, 1-propenyl, 2-propenyl, 2-butenyl, 2-methyl-2-propenyl and 2,3-di-methyl-1,3-butadienyl.

Preferred compounds according to the invention are compounds having formula I, in which $R_1$ is chlorine, bromine or ethyl, and $R_2$ is methyl or ethyl, or a pharmaceutically acceptable salt thereof.

Preferably, Y is HC=CH and X is S, or Y is S and X is $CH_2$.

The most preferred compound has formula I, in which $R_1$ is chlorine, $R_2$ is methyl, X is S, and Y is HC=CH, or a pharmaceutically acceptable salt thereof.

The compounds of the invention can be prepared by methods commonly in use for the preparation of similar known compounds. A suitable method of preparation is the cyclodehydration of an amide of formula II

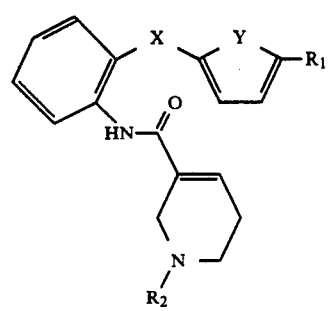

II in which $R_1$, $R_2$, X and Y have the previously given meanings.

This reaction, which is generally known as the Bischler-Napieralski reaction, can be performed by means of condensation agents such as phosphorous pentoxide, zinc chloride, polyphosphoric acid, phosphoryl chloride, or mixtures thereof.

Alternatively an imidoyl halide of the formula III

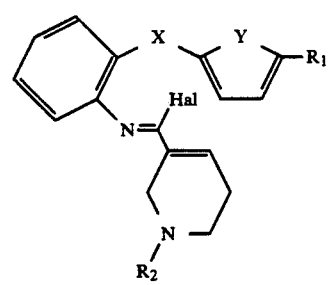

III in which $R_1$, $R_2$, X and Y have the previously given meanings and Hal denotes a halide, and preferably chlorine, is cyclized by means of Lewis acids such as phosphorous pentachloride, zinc chloride, aluminum trichloride, boron trifluoride, or mixtures thereof.

Another method of preparation of compounds of formula I is the reduction of pyridinium derivatives of formula IV

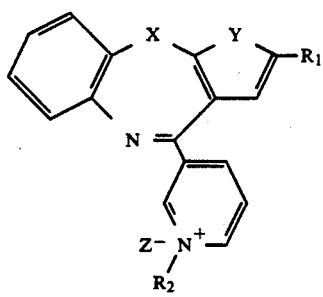

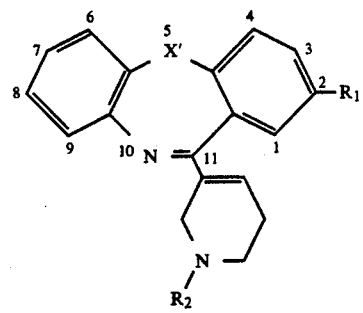

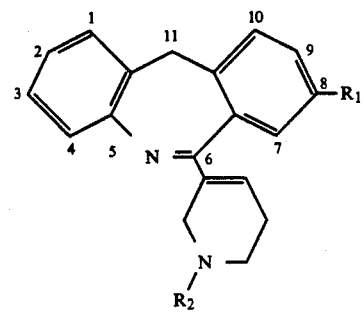

in which $R_1$, $R_2$, X and Y have the previously given meanings and Z is a leaving group, such as a halide (preferably chlorine), or sulphonate. A suitable reduction means is for instance sodium borohydride. Compounds of formula IV can be prepared by reaction of the corresponding pyridinyl derivative V

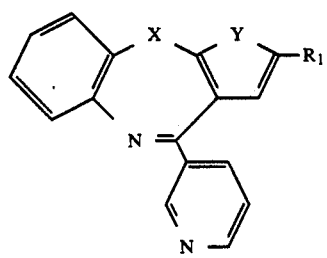

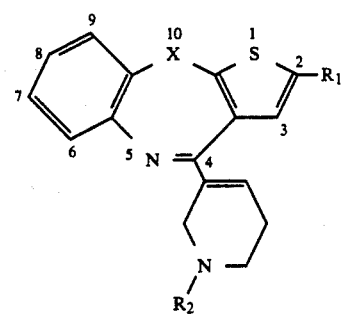

with $R_2$-Z, in which $R_1$, $R_2$, X, Y, and Z have the previously given meanings.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the invention may be administered enterally or parenterally, and for humans preferably in a daily dosage of 0.001-10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

The numbering of the compounds is as follows:

EXAMPLE 1

2-chloro-11-(1,2,5,6-tetrahydro-1-methyl-3-pyridinyl)-dibenzo[b,f][1,4]thiazeoine (E)-2-butenedioate (1:1)

A mixture of 3,7 g of N-[2-(4-chlorophenylthio)-phenyl]-1-methyl-1,2,5,6-tetrahydro-3-pyridinecarboxamide, 37 g of polyphosphoric acid and 3,7 ml of phosphorus oxychloride was heated at 110° C. for 45 minutes. Water was added and the solution was basified with potassium hydroxide. The product was extracted with dichloromethane to give a gum which was crystallized from methanol to give 1,05 g of a product that was converted to the fumarate salt, which on crystallization from methanol gave 2-chloro-11-(1,2,5,6-tetrahydro-1-methyl-3-pyridinyl)dibenzo[b,f][1,4]thiazepine (E)-2-butenedioate (1:1), m.p. 199 .C (dec.).

EXAMPLE 2

In an analogous manner as described in Example 1 were prepared:

8-chloro-6-(1,2,5,6-tetrahydro-1-methyl-3-pyridinyl)-11H-dibenz[b,e]azepine (E)-2-butenedioate (1:1), m.p. 198°-201° C. (dec.).

2-chloro-11-(1,2,5,6-tetrahydro-3-pyridinyl)dibenzo-[b,f][1,4]thiazepine, m.p. 88°-90° C.

2-chloro-11-(1,2,5,6-tetrahydro-1-methyl-3-pyridinyl)-
dibenz[b,f][1,4]oxazepine (E)-2-butenedioate (2:1),
m.p. 175.3° C.

2-bromo-11-(1,2,5,6-tetrahydro-1-methyl-3-pyridinyl)-
dibenzo[b,f][1,4]thiazepine 2,3-dihydroxybutanedio-
ate (2:3), m.p. 124° C. (dec.).

2-bromo-11-(1,2,5,6-tetrahydro-1-methyl-3-pyridinyl)-
dibenz[b,f][1,4]oxazepine 2,3-dihydroxybutanedioate
(2:3), m.p. 160.1° C. (dec.).

2-chloro-11-(1-ethyl-1,2,5,6-tetrahydro-3-pyridinyl)-
dibenzo[b,f][1,4]thiazepine (E)-2-butenedioate (1:1),
m.p. 195°-198° C.

2-ethyl-11-(1,2,5,6-tetrahydro-1-methyl-3-pyridinyl)-
dibenz[b,f][1,4]oxazepine (E)-2-butenedioate (1:1),
m.p. 125.7° C. (dec.).

2-ethyl-11-(1,2,5,6-tetrahydro-1-methyl-3-pyridinyl)-
dibenzo[b,f][1,4]thiazepine (E)-2-butenedioate (1:1),
m.p. 125.1° C. (dec.).

6-(1,2,5,6-tetrahydro-1-methyl-3-pyridinyl)-11H-
dibenz[b,e]azepine (Z)-2-butenedioate (1:1), m.p.
202.8° C.

EXAMPLE 3

In a similar manner as described in Example 1, but using PPE (polyphosphoric ester) instead of polyphosphoric acid and phosphorus oxychloride were prepared:

2-chloro-4-(1,2,5,6-tetrahydro-1-methyl-3-pyridinyl)-
10H-thieno[3,2-]benzazepine ethanedioate (1:1), m.p.
202.4° C.

2-methyl-4-(1,2,5,6-tetrahydro-1-methyl-3-pyridinyl)-
10H-thieno[3,2-c]benzazepine (E)-2-butenedioate
(1:1), m.p. 198.1° C.

2-ethyl-4-(1,2,5,6-tetrahydro-1-methyl-3-pyridinyl)-
thieno[3,2-f]benzo[1,4]thiazepine ethanedioate (1:1).

We claim:

1. A tetrahydropyridinyldibenzazepine derivative of the formula I

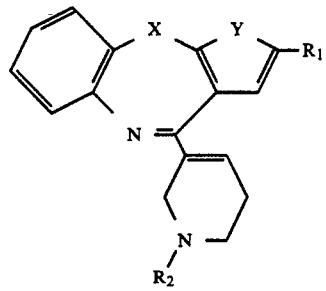

wherein
 $R_1$ is a substituent selected from the group consisting of halogen and lower alkyl;
 $R_2$ is selected from the group consisting of hydrogen, unsubstituted lower alkyl, and unsubstituted or hydroxy substituted lower alkenyl;
 X is O or S;
 Y is HC=CH or S; or a pharmaceutically acceptable salt thereof.

2. The tetrahydropyridinyldibenzazepine derivative of claim 1, wherein $R_1$ is chlorine, bromine or ethyl, and $R_2$ is methyl or ethyl, or a pharmaceutically acceptable salt thereof.

3. The tetrahydropyridinyldibenzazepine derivative of claim 1, wherein Y is HC=CH and X is S, or a pharmaceutically acceptable salt thereof.

4. A tetrahydropyridinyldibenzazepine derivative of the formula

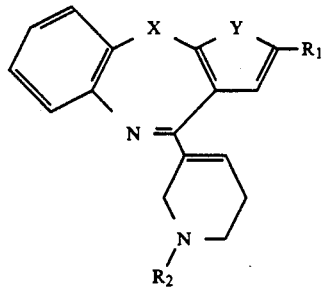

wherein
 $R_1$ is chlorine, $R_2$ is methyl, X is S, and
 Y is HC=CH, or a pharmaceutically acceptable salt thereof.

5. A pharmaceutical preparation comprising an effective amount of the tetrahydropyridinyldibenzazepine derivative of claim 1 for dopamine antagonist activity in admixture with pharmaceutically acceptable auxiliaries.

6. A method of treating dopamine effected psychotic disorders comprising administering to a human patient an effective amount of the tetrahydropyridinyldibenzazepine derivative of claim 1.

* * * * *